United States Patent [19]
Noda

[11] Patent Number: 5,603,928
[45] Date of Patent: Feb. 18, 1997

[54] AIR PURIFICATION AGENT AND PROCESS FOR PRODUCTION OF SAME

[75] Inventor: Tamio Noda, Tokai, Japan

[73] Assignee: Nippon Steel Corporation, Tokyo, Japan

[21] Appl. No.: 295,652

[22] PCT Filed: Jun. 30, 1993

[86] PCT No.: PCT/JP93/00902

§ 371 Date: Aug. 26, 1994

§ 102(e) Date: Aug. 26, 1994

[87] PCT Pub. No.: WO94/14481

PCT Pub. Date: Jul. 7, 1994

[30] Foreign Application Priority Data

Dec. 28, 1992 [JP] Japan ..................... 4-358644

[51] Int. Cl.$^6$ ..................... A61L 9/04
[52] U.S. Cl. ............. 424/76.2; 424/76.3; 424/641; 424/646; 424/682; 424/683
[58] Field of Search ................. 424/76.2, 76.3, 424/641, 683, 682, 646

[56] References Cited

U.S. PATENT DOCUMENTS

| | | | |
|---|---|---|---|
| 4,623,637 | 11/1986 | van der Smissen | 502/333 |
| 4,636,485 | 1/1987 | van der Smissen | 502/66 |
| 5,273,736 | 12/1993 | Nakagawa | 423/702 |

FOREIGN PATENT DOCUMENTS

| | | |
|---|---|---|
| 2217603 | 11/1989 | European Pat. Off. . |
| 0468055 | 1/1992 | European Pat. Off. . |
| 3-228778 | 10/1991 | Japan . |
| 4-180765 | 6/1992 | Japan . |

OTHER PUBLICATIONS

Patent Abstracts of Japan, vol. 15, No. 256 (C-0845), Jun. 28, 1991 & JP-A-03 083 946 (Sumimoto Chem Co Ltd), Apr. 9, 1991.

Database WPI, Section Ch. Week 8137, Derwent Publications Ltd., London, GB; Class E19, An 81-67148 & JP-A-56 095 319 (Matsushita Elec. Ind. KK), Aug. 1, 1981.

*Synth. React. Inorg. Met–Org. Chem.*, vol. 11(3), "Preparation, Characterization and Thermal Properties of Hydrazinium Magnesium Sulfate," by K. C. Patil et al., pp. 245–252, 1981.

*Proc. Indian Acad. Sci.*, vol. 87A (Chemical Sciences–4), No. 8., "Preparation and Characterization of Hydrazinium Derivatives," by K. C. Patil et al., pp. 281–284, Aug., 1978.

*Thermochimica Acta.*, vol. 55, "Thermal Decomposition of Hydrazinium Aluminum Sulfate Hydrate and Hydrazinate," by S. Govindaragan et al., pp. 373–376, 1982.

*Primary Examiner*—Amy Hulina
*Attorney, Agent, or Firm*—Kenyon & Kenyon

[57] ABSTRACT

An air purification agent comprising a salt consisting essentially of hydrazine and one or more metal salts of Ni, Al, Zn, and Ti or comprising a shaped body of chain magnesium silicate as a carrier and a salt consisting essentially of the above metal salt and hydrazine supported thereon, the air purification agent being produced by immersing a chain magnesium silicate in a mixed aqueous solution of the above metal salt and hydrazine, then drying, whereby a salt of the metal salt and hydrazine is supported thereon or by immersing a chain magnesium silicate in an aqueous solution of the metal salt, immersing it in an aqueous solution of hydrazine, then drying, whereby a salt of the metal salt and hydrazine is caused to precipitate to support the same thereon.

3 Claims, 1 Drawing Sheet

AIR PURIFICATION AGENT AND PROCESS FOR PRODUCTION OF SAME

TECHNICAL FIELD

The present invention relates to an air purification agent, and a process for producing the same, for removing acetaldehyde ($CH_3CHO$), formaldehyde (HCHO), trimethylamine (($CH_3$)$_3$N), ammonia ($NH_3$), and other foul smelling or unpleasant smelling substances, from the air.

BACKGROUND ART

Foul smelling gases in the air are treated by the adsorption method using activated carbon, the masking method using other scents, the chemical method for effecting a chemical reaction with, for example, the odorous substances, so as to eliminate or reduce the foul smelling or unpleasant smelling substances. The adsorption method using activated carbon, however, has the problem of degradation of the deodorizing capability in a short time period. Further, since the activated carbon is flammable, there is the disadvantage of its easily becoming a causative factor in fires. In the masking method using other scents, the scents sometimes cause new unpleasantness, and therefore, this cannot be said to be a fundamental solution to the problem. In the chemical method for removal of the foul smelling or unpleasant smelling substances by chemical reactions, there is known, for example, the method of oxidation and decomposition of foul smelling gaseous substances by, for example, ozone, but excessive ozone is harmful to human health, and therefore, there is the problem that a new type of harm is caused. That is, since it is difficult to control the amount of the chemical substance for reacting stoichiometrically with the foul smelling gaseous substance, an unnecessary chemical substance remains and thus this is, again, not a fundamental solution to the problem.

For example, it is difficult to remove acetaldehyde, the main odorous component in cigarette smoke, even using activated carbon. For this purpose, various measures have been taken, such as the improvement of the removal capability by adding the highly chemically reactive aniline to activated carbon, as described in Japanese Unexamined Patent Publication (Kokai) No. 56-53744, and removal by effecting a chemical reaction with phenylhydrazine, as described in Japanese Unexamined Patent Publication (Kokai) No. 56-95319. However, according to the discoveries of the present inventors, the foul smelling odor of the chemically reactive substance itself becomes a problem or the maintenance of the activity of the chemical substance is difficult and the usage life is short. Therefore, these are not fundamental solutions either.

The present inventors previously invented a deodorant composition superior in speed of removal of foul smelling substances such as the four major foul smelling substances of ammonia, trimethylamine, hydrogen sulfide ($H_2S$), and methylmercaptan ($CH_3SH$) and superior in life and proposed the same in Japanese Patent Application No. 3-188939. This uses the reaction product produced by causing contact of, for example, ascorbic acid with a metal such as iron or manganese in a state in the presence of unreacted iron, manganese, etc. This composition can be inexpensively manufactured and features extremely small degradation of the air purifying power with the elapse of time, and therefore, was an improvement over the prior art, but the capability in the removal of aldehyde was of a level requiring further improvement for practical application. In particular, in industry, development of a deodorant which exhibits improved speed of removal of acetaldehyde, formaldehyde, trimethylamine, and ammonia and sustained performance over a long period has been desired.

DISCLOSURE OF THE INVENTION

Accordingly, the object of the present invention is to provide an air purification agent, and a process for producing the same, which further improves and perfects the deodorizing capability of the composition described in Japanese Unexamined Patent Publication (Kokai) No. 3-188939 and is comprised of a new material made by a simple process.

In accordance with the present invention, there is provided an air purification agent comprising a salt consisting essentially of hydrazine and a salt of at least one metal selected from the group consisting of nickel, aluminum, zinc, and titanium.

In accordance with the present invention, there is also provided a process for producing an air purification composition comprising immersing a chain (or linear) magnesium silicate in a mixed aqueous solution of hydrazine and a salt of at least one metal selected from the group consisting of nickel, aluminum, zinc, and titanium and, then drying, whereby a salt consisting essentially of the metal salt and hydrazine is caused to precipitate on the chain magnesium silicate for supporting the same thereon.

BRIEF DESCRIPTION OF THE DRAWINGS

The present invention will now be explained in further detail with reference to the attached FIG. 1.

BEST MODE FOR CARRYING OUT THE INVENTION

Figure 1:
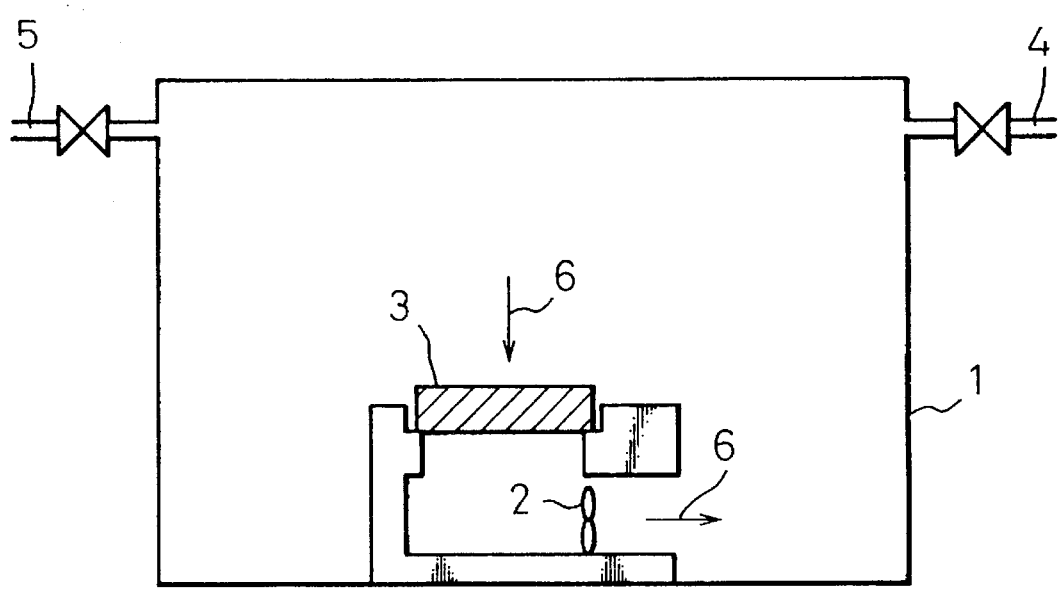
FIG. 1 is an explanatory view showing the construction of a test apparatus for evaluating a deodorizing apparatus.

The present invention relates to an air purification agent which solves the above-mentioned problems and comprises a salt consisting essentially of hydrazine and one or more metal salts of Ni, Al, Zn, and Ti. The present invention relates to an air purification agent comprising a shaped body of chain magnesium silicate as a carrier and the salt consisting essentially of a metal salt and hydrazine supported thereon.

The present invention also relates to a process for producing an air purification composition comprising immersing chain magnesium silicate in a mixed aqueous solution of one or more metal salts of Ni, Al, Zn, and Ti and hydrazine, then drying, or immersing the chain magnesium silicate in an aqueous solution of one or more metal salts of Ni, Al, Zn, and Ti, then immersing it in an aqueous solution of hydrazine, then drying, whereby a salt consisting essentially of the metal salt and hydrazine is caused to precipitate and be supported thereon.

According to the studies of the present inventors, the metal complex of the reaction product between a polybasic acid and metal adsorbs basic gases such as ammonia and trimethylamine extremely well, but the adsorption power with respect to mercaptan gas is poor. One method for solving this problem is to provide a solid base such as described by the present inventors in Japanese Patent Application No. 63-273195 (see Japanese Unexamined Patent Publication (Kokai) No. 3-188939).

However, the present inventors found in the later study that iron hydroxide and ferric oxide produced upon dissolving metal iron in an aqueous solution are substances having strong adsorption power for acidic gases such as hydrogen sulfide. Further, it is found that it was necessary to create a state of copresence of metal iron and iron hydroxide, ferric oxide, and magnetite, to effectively produce iron hydroxide, to keep it stable over a long period, and to sustain its effect. Further, it is found that the efficiency in removing hydrogen sulfide became better and that the efficiency in removing methylmercaptan was also superior.

The reason why the $CH_3SH$ removal efficiency becomes better as the $H_2S$ removal efficiency becomes better is believed to be that the H of the —SH group has similar properties to $H_2S$. Accordingly, it can be deduced that effective production of iron hydroxide is effective for increasing the $CH_3SH$ removal efficiency. However, the present inventors learned from the studies that a good $H_2S$ removal efficiency was not a sufficient condition for a good $CH_3SH$ removal efficiency as well. For example, the reaction product obtained by bringing iron and an aqueous solution of L-ascorbic acid into contact in the air and heat treating the resultant copresent substance of the complex salt and iron at 150° C. for 24 hours is extremely good in $H_2S$ removal efficiency, but is somewhat inferior in $CH_3SH$ removal efficiency.

Various measures for improving the $CH_3SH$ removal efficiency were surveyed and researched. As a result, it was deemed that the $CH_3SH$ removal efficiency was greatly improved by adsorbing hydrogen sulfide on iron oxide. This was proposed previously in Japanese Patent Application No. 3-120473. To develop a composition superior in $CH_3CHO$ removal efficiency, HCHO removal efficiency, $(CH_3)_3N$ removal efficiency, and $NH_3$ removal efficiency, research is required from a completely different perspective. The inventors engaged in a wide range of studies covering metals other than iron as well and thereby succeeded in the development of an air freshener superior in the above various deodorizing performances.

That is, when they tested the deodorizing efficiency of the reaction products between various metal salts and hydrazine, it was confirmed that compositions obtained by causing a reaction between an aqueous solution of one or more metal salts of Ni, Al, Zn, and Ti and hydrazine and drying the double salt of the metal salt and hydrazine produced were superior in $CH_3CHO$ removal efficiency, HCHO removal efficiency, $(CH_3)_3N$ removal efficiency, and $NH_3$ removal efficiency.

Hydrazine is a substance having a strong reducing power and high reactivity. Further, it is a substance which is strong in self decomposition and naturally decomposes into $NH_3$, $N_2$, $H_2$, $H_2O$, etc. or oxidizes, but by making this a double salt with a metal salt, it is increased in chemical stability and the hydrazine can be made to be present stably even for reacting with a gas having a stronger activity. As the gas having a stronger activity, there are $CH_3CHO$ and other aldehydes. These aldehydes have a strong chemical adsorption with hydrazine, and therefore, are taken into the double salt, whereby the air can be purified.

The concentration of the mixture of one or more metal salt selected from sulfates, chlorates, and nitrates of Ni, Al, Zn, and Ti and hydrazine gives the best initial deodorizing efficiency and sustained action, when the metal salt and hydrazine are substantially equal in concentration in terms of the molar concentration converted to metal ions. When away from this, the capability gradually decreases. The reason for this is believed to be that when there is a smaller amount of hydrazine, the interaction between the metal salt and hydrazine becomes too strong and that when there is too much hydrazine, the metal salt is partially reduced and exhibits a catalyst action to promote the decomposition of hydrazine and, also, the pH of the composition is close to the basic side, and therefor the hydrazine easily decomposes. Accordingly, the preferable ratio of the metal salt and hydrazine which is allowed in the present invention is 1:0.5 to 0.5:1 in terms of the molar ratio.

The dried composition comprising the double salt of a metal salt and hydrazine is obtained in a granular or particle form. The powder obtained by crushing the granular composition to under 44 microns has a specific surface area of about 4 $m^2/g$ and can be directly used as a deodorant placed in a bag. Further, a shaped material formed by shaping the powder composition into pellets can be used as the deodorant.

The double salt of the above-mentioned metal salt and hydrazine has a deodorizing property never before seen with respect to several types of sources of foul smelling odors, but to enable it to exhibit its maximum deodorizing, it is effective to increase the specific surface area so as to increase the reaction interface with the foul smelling odor and to increase the flow of air. These two conditions can be satisfied by the use of the supported.

The present invention uses, as a carrier, the relatively inexpensively available chain magnesium silicate. This chain magnesium silicate, for example, sepiolite, palygorskite, etc. are known as natural minerals. In structure, they are mass of magnesium silicate which exhibit a fibrous structure like that of flakes of talc laid together in a brick fashion and have a specific surface area of 230 to 260 $m^2/g$. Sepiolite has numerous pores of 200 Angstrom size, for example. Further, palygorskite has a large number of pores somewhat smaller than sepiolite. These chain magnesium silicates are used as adsorbents. The $CH_3CHO$ removal efficiency of sepiolite particle having 1 to 5 mm size, however, falls to a 50% $CH_3CHO$ removal efficiency after the elapse of 1 month and a 30% $CH_3CHO$ removal efficiency after the elapse of 6 months, and therefore, cannot be said to be sufficient in terms of the deodorizing capability targeted at by the present inventors.

As explained above, chain magnesium silicate has the property of maintaining its porosity while being sintered and, further, has no catalytic action on its own and does not detract from the chemical stability of the supported substance. According to the present invention, there is provided an air purification agent comprising, as a carrier, a shaped body of the chain magnesium silicate, for example, sepiolite crushed to a particle size of 1 to 5 mm or sepiolite particles shaped into a sheet by mixing with a binder or paste or a shaped body of a honeycomb form and having dispersed on the surface of the shaped body or in the pores of the same a double salt of a compound of a metal salt of Ni, Al, Zn, and Ti, alone or combined with each other, and hydrazine.

As the process for producing the above-mentioned air purification agent, there are the process of immersing a shaped body of the chain magnesium silicate, as the support, in an aqueous solution of a mixture of a metal salt and hydrazine, then drying or the process of immersing the shaped body in an aqueous solution of the metal salt, then immersing it in an aqueous solution of hydrazine, and then drying, whereby the double salt of the metal salt and hydrazine is caused to be supported on the surface or in the pores of the chain magnesium silicate.

EXAMPLES

The present invention will now be further explained by, but is by no means limited to, the following Examples.

Example 1

Sepiolite granules having a particle size of 1 to 5 mm were immersed for 1 minute in an aqueous solution comprising a mixture of 0.05 to 1.0 mol/liter of each of an aqueous solution of hydrazine and nickel sulfate, aluminum sulfate, aluminum chloride, ferrous sulfate, zinc sulfate, zinc chloride, titanium sulfate, iron ascorbate, cobalt sulfate, copper sulfate, manganese sulfate, or other metal salts alone or in any mixture thereof, then, after draining, were dried naturally in the atmosphere for 1 month to produce the air purification agent. Typical Examples and Comparative Examples of the mixing conditions of the aqueous solutions are shown in Table 1.

TABLE 1

| | Metal salt | | Reducing agent | | $CH_3CHO$ Removal efficiency % | |
|---|---|---|---|---|---|---|
| No. | Type | Conc. mol/l | Type | Conc. mol/l | after 1 month | % after 6 months |
| 1 | $NiSO_4$ | 0.1 | $N_2H_4$ | 0.1 | 100 | 100 |
| 2 | $Al_2(SO_4)_3$ | 0.1 | $N_2H_4$ | 0.1 | 100 | 100 |
| 3 | $AlCl_3$ | 0.1 | $N_2H_4$ | 0.1 | 100 | 95 |
| 4 | $FeSO_4$ | 0.1 | $N_2H_4$ | 0.1 | 85 | 80 |
| 5 | $FeCl_2$ | 0.1 | $N_2H_4$ | 0.1 | 85 | 75 |
| 6 | $CuSO_4$ | 0.1 | $N_2H_4$ | 0.1 | 25 | — |
| 7 | $ZnSO_4$ | 0.1 | $N_2H_4$ | 0.1 | 90 | 95 |
| 8 | $ZnCl_2$ | 0.1 | $N_2H_4$ | 0.1 | 95 | 90 |
| 9 | $Ti(SO_4)_2$ | 0.1 | $N_2H_4$ | 0.1 | 100 | 100 |
| 10 | Iron L-ascorbate | 0.1 | $N_2H_4$ | 0.1 | 45 | — |
| 11 | $CoSO_4$ | 0.1 | $N_2H_4$ | 0.1 | 20 | — |
| 12 | $MnSO_4$ | 0.1 | $N_2H_4$ | 0.1 | 15 | — |
| 13 | $NiSO_4$ + $FeSO_4$ | 0.2 | $N_2H_4$ | 0.4 | 95 | 90 |
| 14 | $Ti(SO_4)_2$ + $FeSO_4$ | 0.2 | $N_2H_4$ | 0.4 | 80 | 75 |
| 15 | $NiSO_4$ + $Ti(SO_4)_2$ | 0.2 | $N_2H_4$ | 0.4 | 100 | 100 |
| 16 | $Ti(SO_4)_2$ + $ZnSO_4$ | 0.2 | $N_2H_4$ | 0.4 | 100 | 100 |
| 17 | $Al_2(SO_4)_3$ + $ZnSO_4$ | 0.2 | $N_2H_4$ | 0.4 | 100 | 100 |
| 18 | $NiSO_4$ + $Al_2(SO_4)_3$ | 0.2 | $N_2H_4$ | 0.4 | 100 | 100 |
| 19 | $NiSO_4$ + $ZnSO_4$ | 0.2 | $N_2H_4$ | 0.4 | 100 | 100 |
| 20 | $Ti(SO_4)_2$ + $Al_2(SO_4)_3$ | 0.5 | $N_2H_4$ | 1.0 | 100 | 100 |
| 21 | $Al_2(SO_4)_3$ + $FeSO_4$ | 0.5 | $N_2H_4$ | 1.0 | 70 | 60 |
| 22 | $Al_2(SO_4)_3$ + $ZnSO_4$ | 0.5 | $N_2H_4$ | 1.0 | 100 | 100 |
| 23 | $NiSO_4$ + $CoSO_4$ | 0.5 | $N_2H_4$ | 1.0 | 90 | 70 |
| 24 | $NiSO_4$ + $MnSO_4$ | 0.1 | $N_2H_4$ | 0.2 | 85 | 60 |
| 25 | $NiSO_4$ + $CuSO_4$ | 0.1 | $N_2H_4$ | 0.2 | 95 | 65 |
| 26 | $NiSO_4$ | 0.1 | $N_2H_4$ | 0.4 | 95 | 85 |
| 27 | $Al_2(SO_4)_3$ | 0.1 | $N_2H_4$ | 0.4 | 90 | 95 |
| 28 | $ZnSO_4$ | 0.1 | $N_2H_4$ | 0.4 | 85 | 90 |
| 29 | $Ti(SO_4)_2$ + $ZnSO_4$ | 0.5 | $N_2H_4$ | 1.0 | 100 | 100 |
| 30 | $Al_2(SO_4)_3$ + $ZnSO_4$ | 0.5 | $N_2H_4$ | 1.0 | 90 | 90 |

For the deodorizing properties for aldehyde, which is said to be hard for conventional deodorants to handle, evaluation was made of the $CH_3CHO$ removal efficiency. Samples having good capability were then evaluated for the durability thereof as well. The deodorizing test apparatus used is shown in FIG. 1 and composed of a sealed container 1 having an inner volume of 40 liters in which was placed a circulation fan 2 having a capacity of 400 liters/minute. In the Figure, 3 is a filter shaped air purification agent used as the sample, 4 a gas introduction hole, and 5 a gas sampling hole. The gas was circulated in the direction of the arrow 6.

The amount of the deodorant evaluated was 40 g per once. The deodorizing capability was evaluated by packing it in a box of about 90 mm×80 mm×10 mm formed of thick paper at the sides and nonwoven fabric at the top and bottom and placing the box at the fan inlet side. The initial concentration was 100 ppm. The results of evaluations after manufacture 1 month and 6 months are shown in Table 1 as well.

The deodorizing efficiency was obtained by measuring how far the concentration fell after 10 minutes, 20 minutes, and 30 minutes and using the ratio of concentration of the removed gas component. A 100% deodorizing efficiency was achieved in 10 minutes in a certain case, but the Table only shows the values reached after 30 minutes. As is clear from the Table, the deodorant comprises the supported metal according to the present invention exhibits a high deodorizing efficiency, but the effect of improvement of performance in the comparative examples of iron sulfate, iron chloride, iron L-ascorbate, cobalt sulfate, copper sulfate, and manganese sulfate was extremely small. A $CH_3CHO$ removal efficiency was observed by a mixture with the metal salt of the present invention, but in all cases there was tremendous degradation of the performance after the elapse of 6 minutes, and therefore, there were problems with practical use.

Example 2

An evaluation was made using the same type of deodorizers as in Example 1 to check their $(CH_3)_3N$ removal efficiency. The results are shown in Table 2.

TABLE 2

| | Metal salt | | Reducing agent | | $(CH_3)_3N$ Removal efficiency % | |
|---|---|---|---|---|---|---|
| No. | Type | Conc. mol/l | Type | Conc. mol/l | after 1 month | % after 6 months |
| 1 | $NiSO_4$ | 0.1 | $N_2H_4$ | 0.1 | 99 | 99 |
| 2 | $Al_2(SO_4)_3$ | 0.1 | $N_2H_4$ | 0.1 | 100 | 100 |
| 3 | $AlCl_3$ | 0.1 | $N_2H_4$ | 0.1 | 98 | 95 |
| 4 | $FeSO_4$ | 0.1 | $N_2H_4$ | 0.1 | 100 | 100 |
| 5 | $FeCl_2$ | 0.1 | $N_2H_4$ | 0.1 | 100 | 98 |
| 6 | $CuSO_4$ | 0.1 | $N_2H_4$ | 0.1 | 100 | 95 |
| 7 | $ZnSO_4$ | 0.1 | $n_2H_4$ | 0.1 | 99 | 99 |
| 8 | $ZnCl_2$ | 0.1 | $n_2H_4$ | 0.1 | 99 | 95 |
| 9 | $Ti(SO_4)_2$ | 0.1 | $n_2H_4$ | 0.1 | 100 | 100 |
| 10 | Iron L-ascorbate | 0.1 | $N_2H_4$ | 0.1 | 99 | 99 |
| 11 | $CoSO_4$ | 0.1 | $N_2H_4$ | 0.1 | 98 | 97 |
| 12 | $MnSO_4$ | 0.1 | $N_2H_4$ | 0.1 | 95 | 95 |
| 13 | $NiSO_4$ + $FeSO_4$ | 0.2 | $N_2H_4$ | 0.4 | 99 | 99 |
| 14 | $Ti(SO_4)_2$ + $FeSO_4$ | 0.2 | $N_2H_4$ | 0.4 | 99 | 99 |
| 15 | $NiSO_4$ + $Ti(SO_4)_2$ | 0.2 | $N_2H_4$ | 0.4 | 100 | 100 |
| 16 | $Ti(SO_4)_2$ + $ZnSO_4$ | 0.2 | $N_2H_4$ | 0.4 | 100 | 100 |

TABLE 2-continued

| | Metal salt | | Reducing agent | | $(CH_3)_3N$ Removal efficiency % | |
|---|---|---|---|---|---|---|
| No. | Type | Conc. mol/l | Type | Conc. mol/l | after 1 month | % after 6 months |
| 17 | $Al_2(SO_4)_3$ + $ZnSO_4$ | 0.2 | $N_2H_4$ | 0.4 | 100 | 100 |
| 18 | $NiSO_4$ + $Al_2(SO_4)_3$ | 0.2 | $N_2H_4$ | 0.4 | 99 | 99 |
| 19 | $NiSO_4$ + $ZnSO_4$ | 0.2 | $N_2H_4$ | 0.4 | 99 | 99 |
| 20 | $Ti(SO_4)_2$ + $Al_2(SO_4)_3$ | 0.5 | $N_2H_4$ | 1.0 | 100 | 100 |
| 21 | $Al_2(SO_4)_3$ + $FeSO_4$ | 0.5 | $N_2H_4$ | 1.0 | 98 | 99 |
| 22 | $Al_2(SO_4)_3$ + $ZnSO_4$ | 0.5 | $N_2H_4$ | 1.0 | 97 | 99 |
| 23 | $NiSO_4$ + $CoSO_4$ | 0.5 | $N_2H_4$ | 1.0 | 95 | 98 |
| 24 | $NiSO_4$ + $MnSO_4$ | 0.1 | $N_2H_4$ | 0.2 | 95 | 97 |
| 25 | $NiSO_4$ + $CuSO_4$ | 0.1 | $N_2H_4$ | 0.2 | 98 | 100 |
| 26 | $NiSO_4$ | 0.1 | $N_2H_4$ | 0.4 | 95 | 97 |
| 27 | $Al_2(SO_4)_3$ | 0.1 | $N_2H_4$ | 0.4 | 95 | 98 |
| 28 | $ZnSO_4$ | 0.1 | $N_2H_4$ | 0.4 | 95 | 97 |
| 29 | $Ti(SO_4)_2$ + $ZnSO_4$ | 0.5 | $N_2H_4$ | 1.0 | 97 | 100 |
| 30 | $Al_2(SO_4)_3$ + $ZnSO_4$ | 0.5 | $N_2H_4$ | 1.0 | 95 | 98 |

As clear from the Table, the air purification agent supporting thereon the metal according to the present invention exhibits a high deodorizing rate with respect to foul smelling odors of the nitrogen system. Further, a high $(CH_3)_3N$ removal efficiency was seen in the Comparative Example, iron sulfate, iron chloride, iron L-ascorbate, cobalt sulfate, copper sulfate, and manganese sulfate.

INDUSTRIAL APPLICABILITY

According to the present invention, an air purification agent having a high capability in removing $CH_3CHO$, HCHO, $(CH_3)_3N$, and $NH_3$ can be inexpensively and simply produced and the deodorizing performance of the obtained air freshener functions over a long period, so the practical value is high.

I claim:

1. An air purification composition comprising a shaped body of chain magnesium silicate as a carrier, said carrier having disposed thereon a salt consisting essentially of hydrazine and a metal salt of at least one metal selected from a group consisting of nickel, aluminum, zinc, and titanium.

2. A process for producing an air purification composition comprising immersing a chain magnesium silicate in a mixed aqueous solution of hydrazine and a metal salt of at least one metal selected from the group consisting of nickel, aluminum, zinc, and titanium, then drying, whereby a salt consisting essentially of the metal salt and hydrazine is caused to precipitate on the chain magnesium silicate for supporting the same thereon.

3. A process for producing an air purification composition comprising immersing a chain magnesium silicate in an aqueous solution of a metal salt of at least one metal selected from the group consisting of nickel, aluminum, zinc, and titanium, immersing it in an aqueous solution of hydrazine, then drying, whereby a salt consisting essentially of the metal salt and hydrazine is caused to precipitate on the chain magnesium silicate to support the same thereon.

* * * * *